United States Patent
Wang et al.

(10) Patent No.: US 9,922,420 B2
(45) Date of Patent: Mar. 20, 2018

(54) BLOOD PRESSURE MEASURING METHOD AND SYSTEM

(71) Applicant: BOE TECHNOLOGY GROUP CO., LTD., Beijing (CN)

(72) Inventors: Xin Wang, Beijing (CN); Xuelin Han, Beijing (CN); Xiaoli Jin, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 22 days.

(21) Appl. No.: 15/100,480

(22) PCT Filed: Sep. 29, 2015

(86) PCT No.: PCT/CN2015/091033
§ 371 (c)(1),
(2) Date: May 31, 2016

(87) PCT Pub. No.: WO2016/206221
PCT Pub. Date: Dec. 29, 2016

(65) Prior Publication Data
US 2017/0039702 A1   Feb. 9, 2017

(30) Foreign Application Priority Data
Jun. 26, 2015 (CN) .......................... 2015 1 0364594

(51) Int. Cl.
G06K 9/00 (2006.01)
G06T 7/00 (2017.01)
A61B 5/021 (2006.01)

(52) U.S. Cl.
CPC ............ *G06T 7/0012* (2013.01); *A61B 5/021* (2013.01); *G06T 2207/10016* (2013.01)

(58) Field of Classification Search
CPC .............. G06T 7/0012; G06T 7/30104; G06T 7/30201; G06T 2207/10016; A61B 5/021;
(Continued)

(56) References Cited

U.S. PATENT DOCUMENTS 8,208,028 B2 * 6/2012 Yamazaki ................ G07C 1/00
348/143
2008/0275351 A1  11/2008 Kirchberg et al.
(Continued)

FOREIGN PATENT DOCUMENTS

CN  103263271 A  8/2013
CN  103908236 A  7/2014
(Continued)

OTHER PUBLICATIONS

Search Report and Written Opinion dated Mar. 16, 2016 from State Intellectual Property Office of the P.R. China.
(Continued)

*Primary Examiner* — Ali Bayat
(74) *Attorney, Agent, or Firm* — Dilworth & Barrese, LLP.; Michael J. Musella, Esq.

(57) ABSTRACT

A blood pressure measuring method and system. The method includes: obtaining at least one video that captures a first body area and a second body area of a testee; extracting multiple gray scale values for corresponding images that capture the first body area and multiple gray scale values for corresponding images that capture the second body area; drawing a pulse-wave waveform of the first body area based on the multiple gray scale values of the first body area, and drawing a pulse-wave waveform of the second body area based on the multiple gray scale values of the second body area; determining a pulse-wave propagation time based on the pulse-wave waveform of the first body area and the pulse-wave waveform of the second body area; and obtaining a blood pressure value of the testee based on a corresponding relation between the pulse-wave propagation time and blood pressure.

20 Claims, 2 Drawing Sheets

(58) Field of Classification Search
CPC . A61B 5/02116; A61B 5/026; G06K 9/00906
See application file for complete search history.

(56) References Cited

U.S. PATENT DOCUMENTS

| | | |
|---|---|---|
| 2013/0046192 A1 | 2/2013 | Lin et al. |
| 2015/0359714 A1* | 12/2015 | Rabe .................. G06T 7/0012 |
| | | 132/317 |
| 2016/0007865 A1* | 1/2016 | Sakata ................ A61B 5/6898 |
| | | 600/480 |
| 2016/0228011 A1* | 8/2016 | Tsubaki ............... A61B 5/0077 |

FOREIGN PATENT DOCUMENTS

| | | |
|---|---|---|
| CN | 104665803 A | 6/2015 |
| CN | 104887209 A | 9/2015 |
| CN | 204797820 U | 11/2015 |
| WO | 2014136310 A1 | 9/2014 |
| WO | 2014181056 A1 | 11/2014 |

OTHER PUBLICATIONS

Chinese Office Action dated Jun. 1, 2016.
"A Study on Pulse Wave-based Noninvasive Continuous Blood Pressure Measurement Method", PhD Dissertation Full-text Database of China, Medical Science and Technology, Dingli Li, No. 9, 2008, E080-25, Sep. 15, 2008) (refer to line 1 of p. 24 to line 14 of p. 25).
Chinese Office Action dated Feb. 4, 2017.
Third Chinese Office Action dated Jul. 27, 2017.

\* cited by examiner

BLOOD PRESSURE MEASURING METHOD AND SYSTEM

TECHNICAL FIELD

Embodiments of the present disclosure relate to a blood pressure measuring method and system.

BACKGROUND

Currently, in a process of measuring blood pressure of a human body, a mercury sphygmomanometer or an electronic sphygmomanometer is usually adopted to measure the blood pressure. In these two blood pressure measuring approaches, a cuff on the sphygmomanometer is needed to make contact with an arm of the human body to complete the blood pressure measurement. However, when the cuff makes contact with the arm, the accuracy of the measurement result may be low.

SUMMARY

Embodiments of the present disclosure provide a blood pressure measuring method and system, which are used for solving the problem of poor measurement accuracy in a conventional blood pressure measurement when a cuff needs to make contact with an arm of a testee.

At least one embodiment of the present disclosure provides a blood pressure measuring method. The blood pressure measuring method includes: obtaining at least one video that captures a first body area and a second body area of a testee, where each video from the at least one video includes a plurality of frames; extracting, from the frames of the at least one video, a plurality of gray scale values for corresponding images that capture the first body area and a plurality of gray scale values for corresponding images that capture the second body area; drawing a pulse-wave waveform of the first body area based on the plurality of gray scale values for the corresponding images of the first body area, and drawing a pulse-wave waveform of the second body area based on the plurality of gray scale values for the corresponding images of the second body area; determining a pulse-wave propagation time based on the pulse-wave waveform of the first body area and the pulse-wave waveform of the second body area; and obtaining a blood pressure value of the testee based on a corresponding relation between the pulse-wave propagation time and blood pressure.

Besides, at least one embodiment of the present disclosure also provides a blood pressure measuring system. The blood pressure measuring system includes: a video capture device configured to obtain at least one video that captures a first body area and a second body area of a testee, where each video from the at least one video includes a plurality of frames; a gray-scale-value extraction device connected with the video capture device and configured to extract, from the frames of the at least one video, a plurality of gray scale values for corresponding images that capture the first body area and a plurality of gray scale values for corresponding images that capture the second body area; a pulse-wave drawing device connected with the gray-scale-value extraction device and configured to draw a pulse-wave waveform of the first body area based on the plurality of gray scale values for the corresponding images of the first body area and to draw a pulse-wave waveform of the second body area based on the plurality of gray scale values for the corresponding images of the second body area; a pulse-wave-propagation-time determination device connected with the pulse-wave drawing device and configured to determine a pulse-wave propagation time based on the pulse-wave waveform of the first body area and the pulse-wave waveform of the second body area; and a blood-pressure acquisition device connected with the pulse-wave-propagation-time determination device and configured to obtain a blood pressure value of the testee based on a corresponding relation between the pulse-wave propagation time and blood pressure.

BRIEF DESCRIPTION OF THE DRAWINGS

In order to illustrate the technical solutions in the embodiments of the present disclosure or the existing arts more clearly, the drawings need to be used in the description of the embodiments or the existing arts will be briefly described in the following; it is obvious that the drawings described below are only related to some embodiments of the present disclosure, for one ordinary skilled person in the art, other drawings can be obtained according to these drawings.

DETAILED DESCRIPTION

Hereafter, the technical solutions of the embodiments of the present disclosure will be described in a clearly and fully understandable way in connection with the drawings related to the embodiments of the disclosure. It is obvious that the described embodiments are just a part but not all of the embodiments of the present disclosure. The drawings mentioned in the embodiments of the present disclosure are only to exemplarily illustrate the technical solutions of the present disclosure. The other drawings obtained from the drawings of the embodiments of the present disclosure through simple transformations should be within the scope of the present disclosure.

The inventor of the application has noted that when the blood pressure is measured by a mercury sphygmomanometer or an electronic sphygmomanometer, a cuff is used to make contact with the arm, causing blood vessels in the arm to be compressed and physical discomfort of the testee. Consequently, the accuracy of the measurement result of the blood pressure can be affected.

In order to solve the problem of poor measurement accuracy as the cuff needs to make contact with the arm of the testee during the conventional blood pressure measurement, embodiments of the present disclosure provide new technical solutions. Specifically, a pulse-wave waveform of a first body area and a pulse-wave waveform of a second body area are respectively obtained by extraction of gray scale values of corresponding images including the first body area of the testee and extraction of gray scale values of corresponding images including the second body area. Then, a pulse-wave propagation time is determined; and the blood pressure value of the testee is obtained based on the corresponding relation between the pulse-wave propagation time and blood pressure. For instance, in embodiments of the present disclosure, no cuff is needed in the entire process of blood pressure measurement, and the blood pressure of the testee can be measured without contacting the skin of the testee. Since no cuff is needed, the problem that the cuff makes contact with the arm of the testee does not exist any more, and hence the compression of the blood vessels in the arm of the testee via the cuff can be avoided. Consequently, the accuracy of the measurement result of the blood pressure can be improved.

For the convenience of understanding, clear and complete description will be given below to the technical solutions in embodiments of the present disclosure with reference to the accompanying drawings in the embodiments of the present disclosure.

First Embodiment

Figure 1:
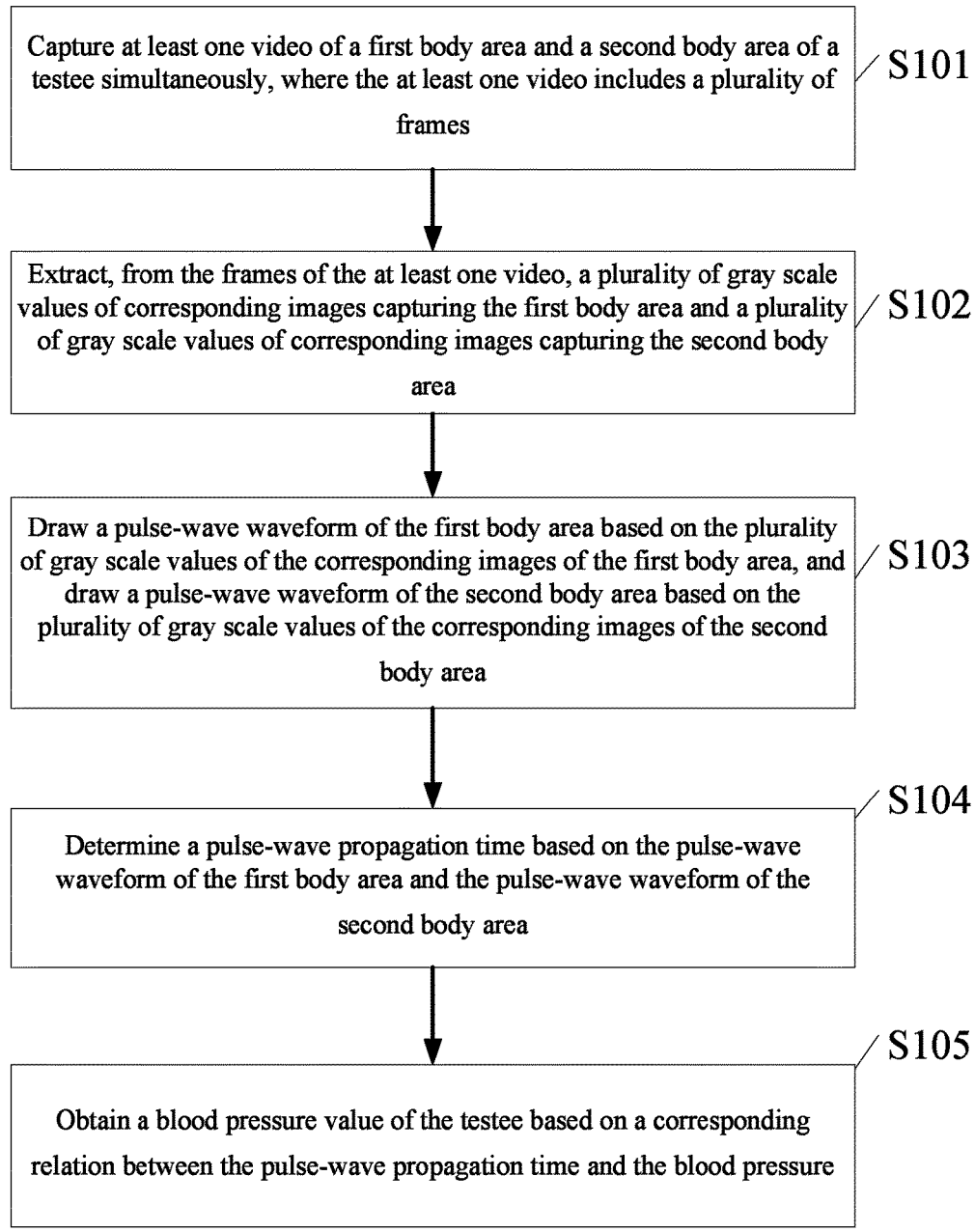
FIG. 1 is a flowchart of a blood pressure measuring method provided by an embodiment of the present disclosure.

The embodiment of the present disclosure provides a blood pressure measuring method. As illustrated in FIG. 1, the blood pressure measuring method includes:

Step S101: capturing at least one video of a first body area and a second body area of a testee simultaneously, where the at least one video includes a plurality of frames.

For instance, at least one video of the face (the first body area) of a testee A and a hand (the second body area) of the testee A is obtained simultaneously.

Step S102: extracting, from the frames of the at least one video, a plurality of gray scale values of corresponding images capturing the first body area and a plurality of gray scale values of corresponding images capturing the second body area.

Step S103: drawing a pulse-wave waveform of the first body area based on the plurality of gray scale values of the corresponding images of the first body area, and drawing a pulse-wave waveform of the second body area based on the plurality of gray scale values of the corresponding images of the second body area.

Step S104: determining a pulse-wave propagation time based on the pulse-wave waveform of the first body area and the pulse-wave waveform of the second body area.

Step S105: obtaining a blood pressure value corresponding to the pulse-wave propagation time based on a corresponding relation between the pulse-wave propagation time and the blood pressure, and taking the blood pressure value as a blood pressure value of the testee.

The first body area and the second body area are two body areas of the testee which have different distances to the heart of the testee. For instance, the first body area is the face area of the testee, and the second body area is the hand area of the testee. A distance between the face area and the heart is different from a distance between the hand area and the heart. Thus, in one aspect, since peripheral capillaries of the face area and the hand area are dense, the measurement accuracy can be high; and in another aspect, since the face area and the hand area are usually exposed and not required to perform other procedures during the measurement (e.g., a step such as undressing), the measurement process can be simple. In addition, during the measurement, the areas are not suppressed by any external object, and physical discomfort of the testee caused by a conventional blood pressure measurement can be avoided. Hence, the accuracy of the measurement results may not be affected.

Detailed description will be given below to the above five steps in the embodiment of the present disclosure.

In the step S101, in order to simultaneously capture the at least one video of the first body area and the second body area of the testee, a plurality of example implementation ways are provided. The embodiment of the present disclosure provides at least two illustrative ways in the following.

A first way includes: filming areas including the first body area and the second body area of the testee using an imaging device. During the blood pressure measurement, the testee may cooperate to perform some actions, so that the first body area and the second body area can be in the same image. Specifically, the first body area and the second body area of the testee may be kept in the same plane and maintain a specific distance, so that both the first body area and the second body area can be within the imaging range at the same time. For instance, when the first body area is the face area of the testee and the second body area is the hand area of the testee, the testee can raise the right hand and place the right hand vertically next to the right ear, with the face and the palm of the right hand facing towards the same direction. When this way is adopted for video capture, the video capture of the first body area and the second body area is carried out simultaneously, and there is no imaging time interval between the first body area and the second body area, leading to high accuracy of blood pressure measurement. In this case, the at least one video includes one video, and each frame of the video includes the face area and the hand area of the testee. Therefore, simultaneously capturing the at least one video of the first body area and the second body area of the testee includes: obtaining images that capture the first body area and the second body area via an imaging device; for example, filming areas including face and a hand of the testee using the same imaging device to generate the video.

A second way includes: filming the first body area of the testee using an imaging device, and simultaneously filming the second body area of the testee using another imaging device. Since two imaging devices are adopted to capture a first video of the first body area and a second video of the second body area of the testee respectively, the testee does not need to perform some actions to keep the first body area and the second body area in the same plane. In this case, for instance, the at least one video includes the first video and the second video; the first video is a video capturing the first body area; and the second video is a video capturing the second body area. Therefore, simultaneously capturing the at least one video of the first body area and the second body area of the testee includes: filming the first body area of the testee using an imaging device to generate the first video, and simultaneously filming the second body area of the testee using another imaging device to generate the second video.

However, it may be difficult to ensure that the video capture of the first body area and the video capture of the second body area are performed simultaneously. In order to solve this problem, the blood pressure measuring method provided by the embodiment of the present disclosure further includes controlling the two imaging devices (namely one imaging device and another imaging device) by triggering signals, so that the two imaging devices perform video capturing simultaneously. Thus, the testee does not need to do some actions to keep the first body area and the second body area in the same plane. Moreover, the simultaneous implementation of the video capture of the first body area and the video capture of the second body area is guaranteed. Thus, there is no imaging time interval between the video capture of the first body area and the video capture of the second body area, and hence the accuracy of blood pressure measurement can be relatively high.

It should be noted that no specific limitation is given to the distance between the testee and the imaging device in the blood pressure measuring method provided by the embodiment of the present disclosure, as long as the distance between the testee and the imaging device can ensure that the first body area and the second body area of the testee can be clearly imaged by the imaging devices. In addition, on the premise of the clear imaging of the first body area and the second body area of the testee, when the first body area and/or the second body area of the testee move back and forth or rotate with a small amplitude, the blood pressure measuring method provided by the embodiment of the present disclosure can also identify the corresponding image of the first body area and the corresponding image of the second body area in each frame.

In addition, in the blood pressure measuring method provided by the embodiment of the present disclosure, when the at least one video of the first body area and the second body area of the testee is simultaneously captured via one or two imaging devices, the one or two imaging devices are high-speed cameras with an imaging frequency greater than or equal to 100 frames per second. The inventor of the application has noted that in actual application the pulse-wave propagation time is about in a magnitude of hundred milliseconds. If a common camera is adopted, the imaging frequency is generally 25 frames per second, and a time interval between two adjacent frames is 40 milliseconds, leading to blood pressure measurement with low accuracy. If the above high-speed camera(s) is adopted, with the imaging frequency being greater than or equal to 100 frames per second, then a maximum time interval between two adjacent frames is 10 milliseconds. Since the time interval between two adjacent frames captured by the high-speed camera is relatively short, the accuracy of blood pressure measurement can be improved.

In order to extract the plurality of gray scale values of the corresponding images including the first body area and the plurality of gray scale values of the corresponding images including the second body area from the frames of the at least one video, the step S102 includes: firstly, identifying a corresponding image of the first body area in each frame of the video of the first body area and a corresponding image of the second body area in each frame of the video of the second body area, the video of the first body area and the video of the second body area being obtained from the step S101; and secondly, extracting one gray scale value of the corresponding image of the first body area in each frame and one gray scale value of the corresponding image of the second body area in each frame, respectively.

As an image has signals in three channels, e.g., red, green and blue, a gray scale value (e.g., a gray scale value of the first body area and/or a gray scale value of the second body area) may be a synthesized gray scale value of the signals in the three channels (e.g., red, green and blue), or may be a gray scale value of a red channel signal. In at least one embodiment of the present disclosure, a gray scale value of a red channel signal in a corresponding image of the first body area and a gray scale value of a red channel signal in a corresponding image of the second body area may be extracted from each frame. Respective extraction of the gray scale values of the red cannel signals from the corresponding image of the first body area and the corresponding image of the second body area has various advantages, which include: as the gray scale value of the red channel signal can reflect a hemoperfusion period more obviously, extraction of the gray scale values of the red channel signals from the corresponding image of the first body area and the corresponding image of the second body area in each frame can improve the accuracy of blood pressure measurement.

It should be noted that: the gray scale value of the corresponding image of the first body area illustrated in the step S102 may be a gray scale value of any test point in the corresponding image of the first body area in each frame, and may also be a mean value of gray scale values of at least two test points in the corresponding image of the first body area. For instance, the gray scale value of the corresponding image of the first body area may be a mean value of gray scale values of all the test points in the corresponding image of the first body area. The gray scale value of the second body area illustrated in the step S102 may be a gray scale value of any test point in the corresponding image of the second body area in each frame, and may also be a mean value of gray scale values of at least two test points in the corresponding image of the second body area. For instance, the gray scale value of the second body area may be a mean value of gray scale values of all the test points in the corresponding image of the second body area. When the gray scale value of the corresponding image of the first body area is the gray scale value of any test point in the corresponding image of the first body area in each frame, the advantage includes that the operation of extracting the gray scale value of the corresponding image of the first body area is relatively simple, and the disadvantage includes that the deviation error is relatively large. When the gray scale value of the corresponding image of the first body area is the mean value of the gray scale values of at least two test points in the corresponding image of the first body area in each frame, the disadvantage includes that the operation of extracting the gray scale value of the corresponding image of the first body area is relatively complex, and the advantage includes that the deviation error is relatively small. For instance, the gray scale value may be selected based on actual needs. Similarly, when the gray scale value of the corresponding image of the second body area is the gray scale value of any test point in the corresponding image of the second body area in each frame, the advantage includes that the operation of extracting the gray scale value of the corresponding image of the second body area is relatively simple, and the disadvantage includes that the deviation error is relatively large. When the gray scale value of the corresponding image of the second body area is the mean value of the gray scale values of at least two test points in the corresponding image of the second body area in each frame, the disadvantage includes that the operation of extracting the gray scale value of the corresponding image of the second body area is relatively complex, and the advantage includes that the deviation error is relatively small. The gray scale value may be selected based on actual needs.

It should be noted that the test point may be one pixel in the corresponding image of the first body area or the corresponding image of the second body area in each frame, and may also be a plurality of adjacent pixels in the corresponding image of the first body area or the corresponding image of the second body area in each frame.

For instance, the at least one video includes one video, and each frame of the video is an image simultaneously including the first body area and the second body area. Extracting the plurality of gray scale values of the corresponding images including the first body area and the plurality of gray scale values of the corresponding images including the second body area from the frames of the at least one video, includes: (1) identifying a corresponding image of the first body area and a corresponding image of the second body area in each frame of the video; and (2) extracting a gray scale value of the corresponding image of the first body area and a gray scale value of the corresponding image of the second body area from each frame of the video. Since the video includes multiple frames and one gray scale value of the corresponding image of the first body area and one gray scale value of the corresponding image of the second body area may be respectively extracted from each frame, multiple gray scale values of corresponding images of the first body area and multiple gray scale values of corresponding images of the second body area may be extracted from the multiple frames of the video respectively. A gray scale value of the corresponding image of the first body area from each frame of the video may be obtained, and the gray scale value may be a gray scale value of any test point in the corresponding image of the first body area or a mean value of the gray scale values of at least two test points in the corresponding image of the first body area. A gray scale value of the corresponding image of the second body area from each frame of the video may be obtained, and the gray scale value may be a gray scale value of any test point in the corresponding image of the second body area or a mean value of the gray scale values of at least two test points in the corresponding image of the second body area.

For instance, the at least one video includes a first video and a second video; the first video is a video of the first body area; and the second video is a video of the second body area. Extracting the plurality of gray scale values of the corresponding images including the first body area and the plurality of gray scale values of the corresponding images including the second body area, includes: (1) identifying a corresponding image of the first body area in each frame of the first video and a corresponding image of the second body area in each frame of the second video; and (2) extracting a gray scale value of the corresponding image of the first body area in each frame of the first video and a gray scale value of the corresponding image of the second body area in each frame of the second video. The first video includes a plurality of frames, and one gray scale value of the corresponding image of the first body area may be extracted from each frame of the first video. Thus, the plurality of gray scale values of the corresponding images of the first body area may be extracted from the plurality of frames of the first video, respectively. The second video includes a plurality of frames, and one gray scale value of the corresponding image of the second body area may be extracted from each frame of the second video. Thus, the plurality of gray scale values of the corresponding images of the second body area may be extracted from the plurality of frames of the second video, respectively. One gray scale value of a corresponding image of the first body area may be obtained from each frame of the first video, and the gray scale value may be a gray scale value of any test point in the corresponding image of the first body area or a mean value of gray scale values of at least two test points in the corresponding image of the first body area. One gray scale value of a corresponding image of the second body area may be obtained from each frame of the second video, and the gray scale value may be a gray scale value of any test point in the corresponding image of the second body area or a mean value of gray scale values of at least two test points in the corresponding image of the second body area.

In the steps S103 and S104, for instance, the pulse-wave waveforms may be drawn by the following manner the pulse-wave waveform of the first body area is drawn by taking the plurality of gray scale values of the corresponding images of the first body area extracted in the step S102 as vertical coordinate values and taking time values as horizontal coordinate values; and the pulse-wave waveform of the second body area is drawn by taking the plurality of gray scale values of the corresponding images of the second body area extracted in the step S102 as vertical coordinate values and taking time values as horizontal coordinate values. The time values can be obtained as follows: if the imaging frequency of an imaging device is set to be f, a time interval of two adjacent frames is 1/f seconds; and a time value corresponding to the 1st frame is selected to be an initial point of time, so that a time value corresponding to the nth frame is (n−1)×1/f seconds. Illustratively, when the imaging frequency of the imaging device is 100 frames per second, a time interval of two adjacent frames is 10 milliseconds, and a time value corresponding to the 10th frame is 90 milliseconds.

Figure 2:
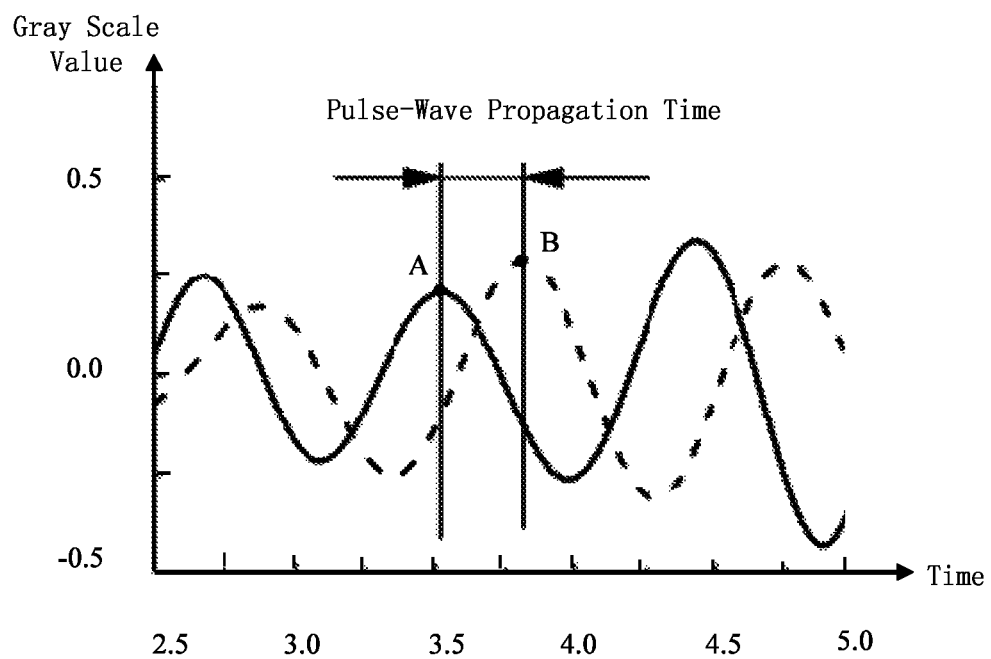
FIG. 2 is a schematic diagram of an example pulse-wave waveform of a first body area and an example pulse-wave waveform of a second body area drawn in an embodiment of the present disclosure.

An example pulse-wave waveform of the first body area and an example pulse-wave waveform of the second body area drawn by the above manner are shown in FIG. 2, where a solid line refers to the pulse-wave waveform of the first body area, and a dotted line refers to the pulse-wave waveform of the second body area. Subsequently, a pulse-wave propagation time is determined based on the pulse-wave waveform of the first body area and the pulse-wave waveform of the second body area. It should be noted that the pulse-wave propagation time refers to a time delay of a pulse wave when propagating at different positions of the body's arteries.

For instance, determining the pulse-wave propagation time based on the pulse-wave waveform of the first body area and the pulse-wave waveform of the second body area, includes: firstly, selecting a wave crest A in the pulse-wave waveform of the first body area and selecting another wave crest B in the pulse-wave waveform of the second body area, where a time interval between the wave crest A and the wave crest B is the shortest; secondly, obtaining the time interval between the wave crest A and the wave crest B; thirdly, obtaining a plurality of time intervals by repeating the above steps for a plurality of times, where wave crests in a plurality of successive cycles in the pulse-wave waveform of the first body area are selected in sequence in the repeating process; and finally, calculating a mean value of the plurality of time intervals obtained in the above step, and taking the mean value as the pulse-wave propagation time.

In the process of determining the pulse-wave propagation time, when only one time interval between adjacent wave crests in one cycle is adopted as the pulse-wave propagation time, the time interval may have deviation error, causing the pulse-wave propagation time to have deviation error, and hence the accuracy of blood pressure measurement can be affected. Therefore, in the embodiment of the present disclosure, the step of obtaining the time interval is repeated for a plurality of times and the mean value of the plurality of time intervals is adopted as the pulse-wave propagation time, so that possible deviation error in the time interval can be reduced, and hence the deviation error in the pulse-wave propagation time can be reduced. Consequently, the accuracy of blood pressure measurement can be improved. It should be noted that the plurality of times refers to two or more times. Ten times is adopted in the embodiment.

In the step S105, as the pulse-wave propagation time can reflect the propagation speed of the pulse wave, the blood pressure can be obtained based on the pulse-wave propagation time. The pulse-wave propagation time, for instance, refers to: there is a time delay when the pulse wave propagates at different positions of the body's arteries, and the delayed time is the pulse-wave propagation time.

Illustratively, the following three formulas are involved in the process of obtaining the blood pressure of the testee based on the relation between the pulse-wave propagation time and the blood pressure:

$$v = \sqrt{\frac{Eh}{\rho d}} \qquad (1)$$

$$E = E_0 e^{\gamma P} \qquad (2)$$

$$v = \frac{S}{PTT} \qquad (3)$$

The relation between the pulse-wave propagation time and the blood pressure, deducted based on the formulas (1), (2) and (3), is as follows:

$$P = \frac{1}{\gamma}\left[\ln\left(\frac{\rho d S^2}{E_0 h}\right) - 2\ln(PTT)\right],$$

where v refers to a propagation speed of the pulse wave; E refers to an elastic modulus of the blood vessels; h refers to a thickness of a vascular wall; d refers to an inner diameter of the vascular wall; ρ refers to a blood viscosity; E0 refers to an elastic modulus of the blood vessels under zero pressure; γ refers to 0.016-0.018 mmHg; S refers to a propagation distance of the pulse wave; and PTT refers to the pulse-wave propagation time. It should be noted that in the relation between the pulse-wave propagation time and the blood pressure, when different body areas are selected in the measuring process, the propagation distance S of the pulse wave may be adjusted to ensure the measurement accuracy. Illustratively, a database on the propagation distances of the pulse wave between different body areas for different body heights and different genders may be established. In the measuring process, a corresponding propagation distance S of the pulse wave may be selected for a testee based on his or her physical condition and different body areas.

In addition, in order to further improve the accuracy of blood pressure measurement, after the step S103, the blood pressure measuring method provided by the embodiment of the present disclosure further includes: filtering the pulse-wave waveform of the first body area and the pulse-wave waveform of the second body area. Illustratively, a Fourier transformation band-pass filter may be adopted. Other interference signals such as jitters caused by respiratory signals and physical stress reactions can be removed by filtering, and hence the accuracy of blood pressure measurement can be improved.

It can be seen from the above embodiment that, by adoption of the blood pressure measuring method provided by the embodiment of the present disclosure, a cuff is not required in the blood pressure measuring process, so that the blood pressure of the testee can be measured without contacting the skin of the testee. Since no cuff is needed, the problem that the cuff makes contact with the arm of the testee does not exist any more, so that compression of the blood vessels in the arm of the testee by the cuff can be avoided. Hence, the accuracy of the measurement result of the blood pressure can be improved. In addition, as no cuff is required, the blood pressure of a testee who has wounds on the arm skin or whose arm is not suitable for wearing the cuff can also be measured by the above blood pressure measuring method.

Second Embodiment

Figure 3:
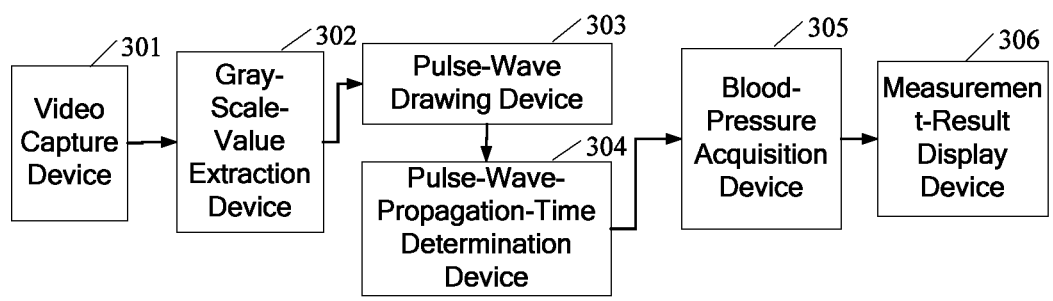
FIG. 3 is a schematic view of a structure of a blood pressure measuring system provided by an embodiment of the present disclosure.

The embodiment of the present disclosure further provides a blood pressure measuring system. As illustrated in FIG. 3, the blood pressure measuring system includes: a video capture device 301; a gray-scale-value extraction device 302 connected with the video capture device 301; a pulse-wave drawing device 303 connected with the gray-scale-value extraction device 302; a pulse-wave-propagation-time determination device 304 connected with the pulse-wave drawing device 303; and a blood-pressure acquisition device 305 connected with the pulse-wave-propagation-time determination device 304.

The working process of the blood pressure measuring system may include: firstly, the video capture device 301 is adopted to obtain a video of a first body area and a video of a second body area of a testee and transmit the obtained videos to the gray-scale-value extraction device 302; the gray-scale-value extraction device 302 is adopted to extract gray scale values of corresponding images of the first body area and gray scale values of corresponding images of the second body area from the videos respectively, and to transmit the gray scale values to the pulse-wave drawing device 303; the pulse-wave drawing device 303 is adopted to respectively draw pulse-wave waveforms of the first body area and the second body area based on corresponding gray scale values, and to transmit the pulse-wave waveforms to the pulse-wave-propagation-time determination device 304; the pulse-wave-propagation-time determination device 304 is adopted to determine the pulse-wave propagation time and transmit the pulse-wave propagation time to the blood-pressure acquisition device 305; and the blood-pressure acquisition device 305 is adopted to obtain a blood pressure value of the testee based on the corresponding relation between the pulse-wave propagation time and the blood pressure.

The first body area and the second body area are two body areas which have different distances to the heart of the testee. In the embodiment of the present disclosure, the first body area is a face area of the testee, and the second body area is a hand area of the testee. The above selection of the body areas has the advantages including that: in one aspect, as peripheral capillaries of the face area and the hand area are dense, the measurement accuracy can be relatively high; and in another aspect, as the face area and the hand area are usually exposed and there is no need to take other procedures during the measurement, e.g., a step such as undressing, the measurement process can be simple.

Detailed description will be given below to the five devices in the embodiment of the present disclosure.

The video capture device 301 is configured to obtain at least one video of the first body area and the second body area of the testee. Each video of the at least one video includes a plurality of frames. The video capture device includes one or more imaging devices.

Illustratively, for the case that the video capture device 301 obtains at least one video of the first body area and the second body area of the testee, the embodiment of the present disclosure provides at least two illustrative ways in the following.

A first way includes: filming areas including the first body area and the second body area of the testee using an imaging device. During the blood pressure measurement, the testee may cooperate to perform some actions, so that the first body area and the second body area can be kept in the same plane. For instance, when the first body area is the face area of the testee and the second body area is the hand area of the testee, the testee can raise the right hand and place the right hand vertically next to the right ear, with the face and the palm of the right hand facing towards the same direction. When this way is adopted for video capture, the video capture of the first body area and the second body area is carried out simultaneously, and there is no imaging time interval between the first body area and the second body area, leading to high accuracy of blood pressure measurement. In this case, the at least one video includes one video, and each frame of the video includes the face area and the hand area of the testee. The video capture device 301 films areas including face and a hand of the testee using the same imaging device to generate the video.

A second way includes: filming the first body area of the testee using an imaging device, and simultaneously filming the second body area of the testee using another imaging device. Since two imaging devices are adopted to capture a video of the first body area and a video of the second body area of the testee respectively, the testee does not need to perform some actions to keep the first body area and the second body area in the same plane. In this case, for instance, the at least one video includes a first video and a second video. The video capture device 301 films the first body area of the testee using an imaging device to generate the first video, and simultaneously films the second body area of the testee using another imaging device to generate the second video.

However, it may be difficult to ensure that the video capture of the first body area and the video capture of the second body area are performed simultaneously. In order to solve this problem, the blood pressure measuring system provided by the embodiment of the present disclosure further includes a trigger-signal control device (not shown in the figures). The trigger-signal control device is configured to control the two imaging devices (namely one imaging device and another imaging device) by triggering signals, so that the two imaging devices perform video capturing simultaneously. Thus, the testee does not need to do some actions to keep the first body area and the second body area in the same plane. Moreover, the simultaneous implementation of the video capture of the first body area and the video capture of the second body area is guaranteed. Thus, there is no imaging time interval between the video capture of the first body area and the video capture of the second body area, and hence the accuracy of blood pressure measurement can be relatively high.

It should be noted that no specific limitation is given to the distance between the testee and the imaging device in the blood pressure measuring system provided by the embodiment of the present disclosure, as long as the distance between the testee and the imaging device can ensure that the first body area and the second body area of the testee can be clearly imaged by the imaging devices. In addition, on the premise of the clear imaging of the first body area and the second body area of the testee, when the first body area and/or the second body area of the testee move back and forth or rotate with a small amplitude, the blood pressure measuring system provided by the embodiment of the present disclosure can also identify the corresponding image of the first body area and the corresponding image of the second body area in each frame.

In addition, the video capture device 301 in the blood pressure measuring system includes one or more imaging devices. The one or more imaging devices are high-speed cameras with an imaging frequency greater than or equal to 100 frames per second. The inventor of the application has noted that in actual application the pulse-wave propagation time is about in a magnitude of hundred milliseconds. If a common camera is adopted, the imaging frequency is generally 25 frames per second, and a time interval between two adjacent frames is 40 milliseconds, leading to blood pressure measurement with low accuracy. If the above high-speed camera(s) is adopted, with the imaging frequency being greater than or equal to 100 frames per second, then a maximum time interval between two adjacent frames is 10 milliseconds. Since the time interval between two adjacent frames captured by the high-speed camera is relatively short, the accuracy of blood pressure measurement can be improved.

For instance, using the gray-scale-value extraction device 302 to extract the plurality of gray scale values of the corresponding images including the first body area and the plurality of gray scale values of the corresponding images including the second body area from each frame, includes: firstly, identifying a corresponding image of the first body area in each frame of a video of the first body area and a corresponding image of the second body area in each frame of a video of the second body area of the testee, the video of the first body area and the video of the second body area being captured by the video capture device 301; and secondly, extracting a gray scale value of the corresponding image of the first body area and a gray scale value of the corresponding image of the second body area from each frame. As an image has signals in three channels, e.g., red, green and blue, a gray scale value may be a synthesized gray scale value of the signals in the three channels (e.g., red, green and blue), or may be a gray scale value of a red channel signal. In embodiments of the present disclosure, a gray scale value of a red channel signal in a corresponding image of the first body area and a gray scale value of a red channel signal in a corresponding image of the second body area may be extracted from each frame. Extraction of the gray scale values of the red cannel signals from the corresponding image of the first body area and the corresponding image of the second body area has various advantages, which include: as the gray scale value of the red channel signal can reflect a hemoperfusion period more obviously, extraction of the gray scale values of the red channel signals from the corresponding image of the first body area and the corresponding image of the second body area in each frame can improve the accuracy of blood pressure measurement.

It should be noted that: the gray-scale-value extraction device 302 may extract a gray scale value of any test point in the corresponding image of the first body area in each frame to be the gray scale value of the corresponding image of the first body area, and may extract a mean value of gray scale values of at least two test points in the corresponding image of the first body area to be the gray scale value of the corresponding image of the first body area. For instance, a mean value of gray scale values of all the test points in the corresponding image of the first body area may be selected as the gray scale value of the corresponding image of the first body area. The gray-scale-value extraction device 302 may extract a gray scale value of any test point in the corresponding image of the second body area in each frame to be the gray scale value of the second body area, and may extract a mean value of gray scale values of at least two test points in the corresponding image of the second body area to be the gray scale value of the second body area. For instance, a mean value of gray scale values of all the test points in the corresponding image of the second body area can be selected as the gray scale value of the second body area.

When the gray scale value of the corresponding image of the first body area is the gray scale value of any test point in the corresponding image of the first body area in each frame, the advantage includes that the operation of extracting the gray scale value of the corresponding image of the first body area is relatively simple, and the disadvantage includes that the deviation error is relatively large. When the gray scale value of the corresponding image of the first body area is the mean value of the gray scale values of at least two test points in the corresponding image of the first body area in each frame, the disadvantage includes that the operation of extracting the gray scale value of the corresponding image of the first body area is relatively complex, and the advantage includes that the deviation error is relatively small. The gray scale value may be selected based on actual needs. Similarly, when the gray scale value of the corresponding image of the second body area is the gray scale value of any test point in the corresponding image of the second body area in each frame, the advantage includes that the operation of extracting the gray scale value of the corresponding image of the second body area is relatively simple, and the disadvantage includes that the deviation error is relatively large. When the gray scale value of the corresponding image of the second body area is the mean value of the gray scale values of at least two test points in the corresponding image of the second body area in each frame, the disadvantage includes that the operation of extracting the gray scale value of the corresponding image of the second body area is relatively complex, and the advantage includes that the deviation error is relatively small. The gray scale value may be selected based on actual needs.

It should be noted that the test point may be one pixel in the corresponding image of the first body area or the corresponding image of the second body area in each frame, and may also be a plurality of adjacent pixels in the corresponding image of the first body area or the corresponding image of the second body area in each frame.

For instance, the at least one video includes one video. The gray-scale-value extraction device 302 extracts the plurality of gray scale values of the corresponding images including the first body area and the plurality of gray scale values of the corresponding images including the second body area from the frames of the at least one video, which includes the following operations: (1) identifying a corresponding image of the first body area and a corresponding image of the second body area in each frame of the video (e.g., each frame of the video includes a corresponding image of the first body area and a corresponding image of the second body area simultaneously); and (2) extracting a gray scale value of the corresponding image of the first body area and a gray scale value of the corresponding image of the second body area from each frame of the video. A gray scale value of the corresponding image of the first body area from each frame of the video may be a gray scale value of any test point in the corresponding image of the first body area, or a mean value of the gray scale values of at least two test points in the corresponding image of the first body area. A gray scale value of the corresponding image of the second body area from each frame of the video may be a gray scale value of any test point in the corresponding image of the second body area, or a mean value of the gray scale values of at least two test points in the corresponding image of the second body area.

For instance, the at least one video includes a first video and a second video; the first video is a video including the first body area; and the second video is a video including the second body area. The gray-scale-value extraction device 302 extracts the plurality of gray scale values of the corresponding images including the first body area and the plurality of gray scale values of the corresponding images including the second body area, which includes the following operations: (1) identifying a corresponding image of the first body area in each frame of the first video and a corresponding image of the second body area in each frame of the second video; and (2) extracting a gray scale value of the corresponding image of the first body area in each frame of the first video and a gray scale value of the corresponding image of the second body area in each frame of the second video. A gray scale value of a corresponding image of the first body area may be a gray scale value of any test point in the corresponding image of the first body area, or a mean value of gray scale values of at least two test points in the corresponding image of the first body area. A gray scale value of a corresponding image of the second body area may be a gray scale value of any test point in the corresponding image of the second body area, or a mean value of gray scale values of at least two test points in the corresponding image of the second body area.

For instance, the pulse-wave drawing device 303 is configured to draw a pulse-wave waveform of the first body area based on the gray scale value of the corresponding image of the first body area in each frame and to draw a pulse-wave waveform of the second body area based on the gray scale value of the corresponding image of the second body area in each frame.

For instance, the pulse-wave drawing device 303 draws the pulse-wave waveforms in the following manner the pulse-wave waveform of the first body area is drawn by taking the plurality of gray scale values of the corresponding images of the first body area extracted by the gray-scale-value extraction device 302 as vertical coordinate values and taking time values as horizontal coordinate values; and the pulse-wave waveform of the second body area is drawn by taking the plurality of gray scale values of the corresponding images of the second body area extracted by the gray-scale-value extraction device 302 as vertical coordinate values and taking time values as horizontal coordinate values. The time values can be obtained as follows: if the imaging frequency of an imaging device is set to be f, a time interval of two adjacent frames is 1/f seconds; and a time value corresponding to the 1st frame is selected to be an initial point of time, so that a time value corresponding to the nth frame is (n−1)×1/f seconds. Illustratively, when the imaging frequency of the imaging device is 100 frames per second, a time interval of two adjacent frames is 10 milliseconds, and a time value corresponding to the 10th frame is 90 milliseconds. An example pulse-wave waveform of the first body area and an example pulse-wave waveform of the second body area drawn by the above manner are shown in FIG. 2, where a solid line refers to the pulse-wave waveform of the first body area, and a dotted line refers to the pulse-wave waveform of the second body area.

For example, the pulse-wave-propagation-time determination device 304 is configured to determine a pulse-wave propagation time based on the pulse-wave waveform of the first body area and the pulse-wave waveform of the second body area.

It should be noted that the pulse-wave propagation time, for instance, refers to: there is a time delay when the pulse wave propagates at different positions of the body's arteries, and the delayed time is the pulse-wave propagation time.

In the blood pressure measuring system provided by the embodiment of the present disclosure, as illustrated in FIG. 2, the step of determining the pulse-wave propagation time based on the pulse-wave waveform of the first body area and the pulse-wave waveform of the second body area via the pulse-wave-propagaation-time determination device 304 may include:

firstly, selecting one wave crest A in the pulse-wave waveform of the first body area and selecting another wave crest B in the pulse-wave waveform of the second body area, where the time interval between the wave crest A and the wave crest B is the shortest;

secondly, obtaining the time interval between the wave crest A and the wave crest B;

thirdly, obtaining a plurality of time intervals by repeating the above steps for a plurality of times, where wave crests in a plurality of successive cycles in the pulse-wave waveform of the first body area are selected in sequence in the repeating process; and finally, calculating a mean value of the plurality of time intervals obtained in the above step, and taking the mean value as the pulse-wave propagation time.

In the process of determining the pulse-wave propagation time, when only the time interval between adjacent wave crests in one cycle is adopted as the pulse-wave propagation time, the time interval may have deviation error, causing the pulse-wave propagation time to have deviation error, and hence the accuracy of blood pressure measurement can be affected. Therefore, in the embodiment of the present disclosure, the step of obtaining the time interval is repeated for a plurality of times and the mean value of the plurality of time intervals is adopted as the pulse-wave propagation time, so that possible deviation error in the time interval can be reduced, and hence the deviation error in the pulse-wave propagation time can be reduced. Consequently, the accuracy of blood pressure measurement can be improved. It should be noted that the plurality of times refers to two or more times. Ten times is adopted in the embodiment.

For instance, the blood-pressure acquisition device 305 is configured to obtain a blood pressure value of the testee based on the relation between the pulse-wave propagation time and the blood pressure. As the pulse-wave propagation time can reflect the propagation speed of the pulse wave, the blood pressure can be obtained based on the pulse-wave propagation time. The pulse-wave propagation time, for instance, refers to: a time delay of the pulse wave when propagating at different positions of the body's arteries.

Illustratively, the following three formulas may be involved in the process of obtaining the blood pressure value of the testee based on the relation between the pulse-wave propagation time and the blood pressure:

$$v = \sqrt{\frac{Eh}{\rho d}} \quad (1)$$

$$E = E_0 e^{\gamma P} \quad (2)$$

$$v = \frac{S}{PTT} \quad (3)$$

The relation between the pulse-wave propagation time and the blood pressure, deducted based on the formulas (1), (2) and (3), is as follows:

$$P = \frac{1}{\gamma}\left[\ln\left(\frac{\rho d S^2}{E_0 h}\right) - 2\ln(PTT)\right],$$

where v refers to a propagation speed of the pulse wave; E refers to an elastic modulus of the blood vessels; h refers to a thickness of a vascular wall; d refers to an inner diameter of the vascular wall; $\rho$ refers to a blood viscosity; E0 refers to an elastic modulus of the blood vessels under zero pressure; $\gamma$ refers to 0.016-0.018 mmHg; S refers to a propagation distance of the pulse wave; and PTT refers to the pulse-wave propagation time. It should be noted that in the relation between the pulse-wave propagation time and the blood pressure, when different body areas are selected in the measuring process, the propagation distance S of the pulse wave may be adjusted to ensure the measurement accuracy. Illustratively, a database on the propagation distances of the pulse wave between different body areas for different body heights and different genders may be established. In the measuring process, a corresponding propagation distance S of the pulse wave may be selected for a testee based on his or her physical condition and different body areas.

According to actual application needs, as illustrated in FIG. 3, the blood pressure measuring system provided by the embodiment of the present disclosure may further include a measurement-result display device 306 which is configured to display the measurement result of the blood pressure, so that the testee can intuitively known the measurement result of the blood pressure. Illustratively, the measurement-result display device 306 may be a liquid crystal display device.

In addition, in order to further improve the accuracy of blood pressure measurement, the blood pressure measuring system provided by the embodiment of the present disclosure further includes a filtering device. The filtering device is configured to filter the pulse-wave waveform of the first body area and the pulse-wave waveform of the second body area drawn by the pulse-wave drawing device 303. Illustratively, the filtering device may adopt a Fourier transformation band-pass filter to filter the pulse-wave waveform of the first body area and the pulse-wave waveform of the second body area. Other interference signals such as jitters caused by respiratory signals and physical stress reactions can be removed by filtering, and hence the accuracy of blood pressure measurement can be improved.

It can be seen from the above embodiment that, by adoption of the blood pressure measuring system provided by the embodiment of the present disclosure, a cuff is not required in the blood pressure measuring process, so that the blood pressure of the testee can be measured without contacting the skin of the testee. Since no cuff is needed, the problem that the cuff makes contact with the arm of the testee does not exist any more, so that compression of the blood vessels in the arm of the testee by the cuff can be avoided. Hence, the accuracy of the measurement result of the blood pressure can be improved. In addition, as no cuff is required, the blood pressure of a testee who has wounds on the arm skin or whose arm is not suitable for wearing the cuff can also be measured by the above blood pressure measuring method.

Embodiments in the description are illustrated by a progressive approach; same or similar parts of the embodiments may be referred to each other; and the description of each embodiment includes differences from other embodiments. Particularly for the system embodiment, as the system embodiment is similar to the method embodiment, the description is relatively simple, and relevant description may be referred to the description of the method embodiment.

The blood pressure measuring system provided by the embodiment of the present disclosure may further include one or more processors and one or more memories. The processor may process data signals and may include various computing architectures such as a complex instruction set computer (CISC) architecture, a reduced instruction set computer (RISC) architecture or an architecture for implementing a combination of multiple instruction sets. The memory may store instructions and/or data executed by the processor. The instructions and/or data may include codes which are configured to achieve some functions or all the functions of one or more devices in the embodiments of the present disclosure. For instance, the memory includes a dynamic random access memory (DRAM), a static random access memory (SRAM), a flash memory, an optical memory or other memories well known to those skilled in the art.

In some embodiments of the present disclosure, the gray-scale-value extraction device, the pulse-wave drawing device, the pulse-wave-propagation-time determination device and/or the blood-pressure acquisition device include codes and programs stored in the memories; and the processors may execute the codes and the programs to achieve some functions or all the functions of the gray-scale-value extraction device, the pulse-wave drawing device, the pulse-wave-propagation-time determination device and/or the blood-pressure acquisition device.

In some embodiments of the present disclosure, the gray-scale-value extraction device, the pulse-wave drawing device, the pulse-wave-propagation-time determination device and/or the blood-pressure acquisition device may be specialized hardware devices and configured to achieve some or all the functions of the gray-scale-value extraction device, the pulse-wave drawing device, the pulse-wave-propagation-time determination device and/or the blood-pressure acquisition device. For instance, the gray-scale-value extraction device, the pulse-wave drawing device, the pulse-wave-propagation-time determination device and/or the blood-pressure acquisition device may be a circuit board or a combination of a plurality of circuit boards and configured to achieve the above functions. In embodiments of the present disclosure, the circuit board or a combination of the plurality of circuit boards may include: (1) one or more processors; (2) one or more non-transitory computer-readable memories connected with the processors; and (3) processor-executable firmware stored in the memories.

It should be noted that, in the drawings, the size of a layer or an area may be exaggerated for clarity of the drawings. Besides, it is understandable that if an element or a layer is said to be "under" another element or layer, it can be directly under the other element or an intermediate layer may exist therebetween. Besides, it is understandable that if a layer or an element is said to be "between" two layers or "between" two elements, it can be the only one layer or element between the two layers or two elements, or one or more intermediate layer or element can exist. Similar reference marks in the full text refer to the similar elements.

In the present disclosure, the terms "first," "second," "third", etc. are not intended to indicate or imply any importance, but merely used for description purposes. The term "plurality" refers to two or more than two, unless otherwise defined. The terms "comprises," "comprising," "includes," "including," etc., are intended to specify that the elements or the objects stated before these terms encompass the elements or the objects and equivalents thereof listed after these terms, but do not preclude the other elements or objects.

It should be note that "on," "under," "right," "left" and the like are only used to indicate relative position relationship, and when the position of the object which is described is changed, the relative position relationship may be changed accordingly. The phrases "connect", "connected", etc., are not intended to define a physical connection or mechanical connection, but may include an electrical connection, directly or indirectly.

The foregoing are merely specific embodiments of the disclosure, but not limitative to the protection scope of the disclosure. One skilled in the art could devise variations or replacements that within the scope and the spirit of the present disclosure, those variations or replacements shall belong to the protection scope of the disclosure. Thus, the protection scope of the disclosure shall be defined by the accompanying claims.

The present disclosure claims the benefits of Chinese patent application No. 201510364594.9, which was filed on Jun. 26, 2015 and is incorporated herein in its entirety by reference as part of this application.

What is claimed is:

1. A blood pressure measuring method, comprising:
   obtaining at least one video that captures a first body area and a second body area of a testee, wherein each video from the at least one video includes a plurality of frames;
   extracting, from the frames of the at least one video, a plurality of gray scale values for corresponding images that capture the first body area and a plurality of gray scale values for corresponding images that capture the second body area;
   drawing a pulse-wave waveform of the first body area based on the plurality of gray scale values for the corresponding images of the first body area, and drawing a pulse-wave waveform of the second body area based on the plurality of gray scale values for the corresponding images of the second body area;
   determining a pulse-wave propagation time based on the pulse-wave waveform of the first body area and the pulse-wave waveform of the second body area; and
   obtaining a blood pressure value of the testee based on a corresponding relation between the pulse-wave propagation time and blood pressure,
   wherein extracting, from the frames of the at least one video, the plurality of gray scale values for corresponding images that capture the first body area and the plurality of gray scale values for corresponding images that capture the second body area, includes:
      identifying the corresponding images of the first body area and the corresponding images of the second body area from frames of the at least one video; and
      extracting a plurality of gray scale values of a red channel signal in the corresponding images of the first body a plurality of gray scale values of the red channel signal in the corresponding images of the second body area from the frames of the at least one video.

2. The blood pressure measuring method according to claim 1, wherein:
   the at least one video includes one video; and
   obtaining at least one video that captures the first body area and the second body area of the testee includes:
      filming areas including face and a hand of the testee using an imaging device to generate the video.

3. The blood pressure measuring method according to claim 1, wherein:
   the at least one video includes a first video and a second video; and
   obtaining at least one video that captures the first body area and the second body area of the testee includes:
      filming the first body area of the testee using an imaging device to generate the first video, and simultaneously filming the second body area of the testee using another imaging device to generate the second video.

4. The blood pressure measuring method according to claim 2, wherein the imaging device is a high-speed camera with an imaging frequency greater than or equal to 100 frames per second.

5. The blood pressure measuring method according to claim 1, wherein:
the at least one video includes one video; and
extracting, from the frames of the at least one video, the plurality of gray scale values for corresponding images that capture the first body area and the plurality of gray scale values for corresponding images that capture the second body area, further includes:
identifying a corresponding image of the first body area and a corresponding image of the second body area from each frame of the video; and
extracting a gray scale value of the red channel signal in the corresponding image of the first body area and a gray scale value of the red channel signal in the corresponding image of the second body area from each frame of the video.

6. The blood pressure measuring method according to claim 5, wherein:
each gray scale value of the corresponding image of the first body area is a gray scale value of any test point in the corresponding image of the first body area in one corresponding frame of the video, or a mean value of gray scale values of at least two test points in the corresponding image of the first body area; and
each gray scale value of the corresponding image of the second body area is a gray scale value of any test point in the corresponding image of the second body area in one corresponding frame of the video, or a mean value of gray scale values of at least two test points in the corresponding image of the second body area.

7. The blood pressure measuring method according to claim 1, wherein:
the at least one video includes a first video and a second video; and
extracting, from the frames of the at least one video, the plurality of gray scale values for corresponding images that capture the first body area and the plurality of gray scale values for corresponding images that capture the second body area, further includes:
identifying a corresponding image of the first body area in each frame of the first video and a corresponding image of the second body area in each frame of the second video; and
extracting a gray scale value of the red channel signal in the corresponding image of the first body area from each frame of the first video and a gray scale value of the red channel signal in the corresponding mage of the second body area from each frame of the second video.

8. The blood pressure measuring method according to claim 7, wherein:
each gray scale value of the corresponding image of the first body area is a gray scale value of any test point in the corresponding image of the first body area in one corresponding frame of the first video, or a mean value of gray scale values of at least two test points in the corresponding image of the first body area; and
each gray scale value of the corresponding image of the second body area is a gray scale value of any test point in the corresponding image of the second body area in one corresponding frame of the second video, or a mean value of gray scale values of at least two test points in the corresponding image of the second body area.

9. The blood pressure measuring method according to claim 1, wherein determining the pulse-wave propagation time based on the pulse-wave waveform of the first body area and the pulse-wave waveform of the second body area, includes:
selecting a wave crest in the pulse-wave waveform of the first body area, and selecting another wave crest, which has a shortest time interval to the wave crest, in the pulse-wave waveform of the second body area;
obtaining the time interval between the wave crest and the other wave crest;
obtaining a plurality of time intervals by repeating the above operations for a plurality of times, wherein wave crests in a plurality of successive cycles in the pulse-wave waveform of the first body area are selected in sequence in the repeating process; and
calculating a mean value of the plurality of time intervals as the pulse-wave propagation time.

10. The blood pressure measuring method according to claim 1, wherein the relation between the pulse-wave propagation time and the blood pressure is as follows:

$$P = \frac{1}{\gamma}\left[\ln\left(\frac{\rho dS^2}{E_0 h}\right) - 2\ln(PTT)\right],$$

wherein h refers to a thickness of a vascular wall; d refers to an inner diameter of the vascular wall; S refers to a propagation distance of the pulse-wave; $\rho$ refers to a blood viscosity; E0 refers to an elastic modulus of blood vessels under zero pressure; $\gamma$ refers to 0.016-0.018 mmHg; and PTT refers to the pulse-wave propagation time.

11. The blood pressure measuring method according to claim 1, wherein after drawing the pulse-wave waveform of the first body area based on the plurality of gray scale values for the corresponding images of the first body area, and drawing the pulse-wave waveform of the second body area based on the plurality of gray scale values for the corresponding images of the second body area, the blood pressure measuring method further comprises:
filtering the pulse-wave waveform of the first body area and the pulse-wave waveform of the second body area.

12. A blood pressure measuring system, comprising:
a video capture device configured to obtain at least one video that captures a first body area and a second body area of a testee, wherein each video from the at least one video includes a plurality of frames;
a processor; and
a memory that stores instructions, wherein the instructions, when executed by the processor, cause the processor to perform operations including:
extracting, from the frames of the at least one video, a plurality of gray scale values for corresponding images that capture the first body area and a plurality of gray scale values for corresponding images that capture the second body area;
drawing a pulse-wave waveform of the first body area based on the plurality of gray scale values for the corresponding images of the first body area and to draw a pulse-wave waveform of the second body area based on the plurality of gray scale values for the corresponding images of the second body area;

determining a pulse-wave propagation time based on the pulse-wave waveform of the first body area and the pulse-wave waveform of the second body area; and obtaining a blood pressure value of the testee based on a corresponding relation between the pulse-wave propagation time and blood pressure, wherein the instructions when executed by the processor cause the processor to extract, from the frames of the at least one video, the plurality of gray scale values for corresponding images that capture the first body area and the plurality of gray scale values for corresponding images that capture the second body area at least by:

identifying the corresponding images of the first body area and the corresponding images of the second body area from frames of the at least one video; and extracting a plurality of gray scale values of a red channel signal in the corresponding images of the first body area and a plurality of gray scale values of the red channel signal in the corresponding images of the second body area from the frames of the at least one video.

13. The blood pressure measuring system according to claim 12, wherein the at least one video includes one video; and the video capture device is an imaging device which is configured to film areas including face and a hand of the testee to generate the video.

14. The blood pressure measuring system according to claim 13, wherein the imaging device is a high-speed camera with an imaging frequency greater than or equal to 100 frames per second.

15. The blood pressure measuring system according to claim 12, wherein the at least one video includes one video; and the instructions when executed by the processor cause the processor to extract, from the frames of the at least ore video, the plurality of gray scale values for corresponding images that capture the first body area and the plurality of gray scale values for corresponding images that capture the second body area further at least by:

identifying a corresponding image of the first body area and a corresponding image of the second body area from each frame of the video; and extracting a gray scale value of the red channel signal in the corresponding image of the first body area and a gray scale value of a the red channel signal in the corresponding image of the second body area from each frame of the video.

16. The blood pressure measuring system according to claim 12, wherein the at least one video includes a first video and a second video; and the video capture device includes a first imaging device and a second imaging device which are configured to film the first body area and the second body area of the testee simultaneously to generate the first video and the second video, respectively.

17. The blood pressure measuring system according to claim 16, wherein wherein the instructions when executed by the processor cause the processor to extract, from the frames of the at least one video, the plurality of gray scale values for corresponding images that capture the first body area and the plurality of gray scale values for corresponding images that capture the second body area further at least by:

identifying a corresponding image of the first body area in each frame of the first video and a corresponding image of the second body area in each frame of the second video; and extracting a gray scale value of the red channel signal in the corresponding image of the first body area from each frame of the first video and a gray scale value of the red channel signal in the corresponding mage of the second body area from each frame of the second video.

18. The blood pressure measuring system according to claim 17, wherein the instructions when executed by the processor cause the processor to extract, from the frames of the at least one video, the plurality of gray scale values for corresponding images that capture the first body area and the plurality of gray scale values for corresponding images that capture the second body area further at least by:

extracting a gray scale value of any test point in the corresponding image of the first body area from each frame of the first video to be the corresponding gray scale value of the corresponding image of the first body area, or extracting a mean value of gray scale values of at least two test points in the corresponding image of the first body area from each frame of the first video to be the corresponding gray scale value of the corresponding image of the first body area; and extracting a gray scale value of any test point in the corresponding image of the second body area from each frame of the second video to be the corresponding gray scale value of the corresponding image of the second body area, or extracting a mean value of gray scale values of at least two test points in the corresponding image of the second body area from each frame of the second video to be the corresponding gray scale value of the corresponding image of the second body area.

19. The blood pressure measuring system according to claim 12, wherein the instructions when executed by the processor causes the processor to determine the pulse-wave propagation time based on the pulse-wave waveform of the first body area and the pulse-wave waveform of the second body area at least by:

selecting a wave crest in the pulse-wave waveform of the first body area, and selecting another wave crest, which has a shortest time interval to the wave crest, in the pulse-wave waveform of the second body area;

obtaining the time interval between the wave crest and the other wave crest;

obtaining a plurality of time intervals by repeating the above operations for a plurality of times, wherein wave crests in a plurality of successive cycles in the pulse-wave waveform of the first body area are selected in sequence in the repeating process; and calculating a mean value of the plurality of time intervals as the pulse-wave propagation time.

20. The blood pressure measuring system according to claim 12, wherein the blood pressure measuring system further comprises a filtering device which is configured to filter the pulse-wave waveform of the first body area and the pulse-wave waveform of the second body area.

* * * * *